(12) United States Patent
Steed et al.

(10) Patent No.: US 11,253,667 B2
(45) Date of Patent: Feb. 22, 2022

(54) CUSHION MEMBER AND METHOD OF MANUFACTURING SAME

(71) Applicant: KONINKLIJKE PHILIPS N.V., Eindhoven (NL)

(72) Inventors: Daniel Steed, North Huntingdon, PA (US); Adam LeVern Bell, Pittsburgh, PA (US); Robert Edward O'Grady, Pittsburgh, PA (US); Jonathan Paul McCaslin, Renfrew, PA (US)

(73) Assignee: Koninklijke Philips N.V., Eindhoven (NL)

( * ) Notice: Subject to any disclaimer, the term of this patent is extended or adjusted under 35 U.S.C. 154(b) by 543 days.

(21) Appl. No.: 16/306,172

(22) PCT Filed: Jun. 1, 2017

(86) PCT No.: PCT/EP2017/063236
§ 371 (c)(1),
(2) Date: Nov. 30, 2018

(87) PCT Pub. No.: WO2017/207676
PCT Pub. Date: Dec. 7, 2017

(65) Prior Publication Data
US 2021/0220597 A1    Jul. 22, 2021

Related U.S. Application Data

(60) Provisional application No. 62/345,030, filed on Jun. 3, 2016.

(51) Int. Cl.
*A61M 16/06* (2006.01)
*B29D 99/00* (2010.01)

(52) U.S. Cl.
CPC ..... *A61M 16/0622* (2014.02); *B29D 99/0071* (2013.01); *A61M 2205/0216* (2013.01); *A61M 2207/00* (2013.01)

(58) Field of Classification Search
CPC .... A61M 11/002; A61M 11/06; A61M 16/06; A61M 16/0605; A61M 16/0616;
(Continued)

(56) References Cited

U.S. PATENT DOCUMENTS

| | | | | |
|---|---|---|---|---|
| 5,603,314 A | * | 2/1997 | Bono | A61M 11/06 128/200.14 |
| 6,068,459 A | * | 5/2000 | Clarke | F04C 27/005 418/55.4 |

(Continued)

FOREIGN PATENT DOCUMENTS

| | | |
|---|---|---|
| DE | 102009038655 A1 | 2/2011 |
| WO | WO2009026627 A1 | 3/2009 |

(Continued)

*Primary Examiner* — Annette Dixon
(74) *Attorney, Agent, or Firm* — Michael W. Haas

(57) ABSTRACT

A cushion member (10) for a mask structured to be worn on a face of a user. The cushion member includes a cushion portion (12) having a sealing portion (13) and a body portion (14) extending from the sealing portion, the sealing portion being structured to engage the face of the user; and at least one mesh member (22) embedded in at least one of the sealing portion and the body portion.

13 Claims, 6 Drawing Sheets

(58) Field of Classification Search
CPC .......... A61M 16/0666; A61M 16/0683; A61M 16/0694; A61M 16/0833; A61M 16/1055; A61M 16/107; A61M 16/1075; A61M 16/16; A61M 16/161; A61M 16/208; A61M 2016/0027; A61M 2016/0036; A61M 2205/0227; A61M 2205/3368; A61M 2205/581; A61M 2205/582; A61M 2205/583; A61M 2205/588; A61M 2210/0618; A61M 2210/0625; H04R 1/1083; H04R 5/0335; Y10S 128/909; Y10S 128/91

See application file for complete search history.

(56) References Cited

U.S. PATENT DOCUMENTS

| | | | |
|---|---|---|---|
| 6,152,137 | A | 11/2000 | Schwartz |
| 2008/0047560 | A1* | 2/2008 | Veliss ............... A61M 16/0605 128/206.24 |
| 2010/0229868 | A1 | 9/2010 | Rummery |
| 2015/0151066 | A1 | 6/2015 | Chodkowski |
| 2017/0326320 | A1* | 11/2017 | Baigent ............. A61M 16/0616 |

FOREIGN PATENT DOCUMENTS

| | | |
|---|---|---|
| WO | WO2009052560 A1 | 4/2009 |
| WO | WO20100148453 A1 | 12/2010 |
| WO | WO2013084109 A1 | 6/2013 |
| WO | WO2015147947 A2 | 10/2015 |

* cited by examiner

CUSHION MEMBER AND METHOD OF MANUFACTURING SAME

CROSS-REFERENCE TO RELATED APPLICATIONS

This patent application claims the priority benefit under 35 U.S.C. § 371 of international patent application no PCT/EP2017/063236, filed Jun. 1, 2017, which claims the priority benefit under 35 U.S.C. § 119(e) of U.S. Provisional Application No. 62/345,030 filed on Jun. 3, 2016, the contents of which are herein incorporated by reference.

BACKGROUND OF THE INVENTION

1. Field of the Invention

The present invention relates to non-invasive ventilation and pressure support systems wherein a mask is used to deliver a flow of breathing gas to a user, and in particular to cushion members for such masks. The present invention is also related to methods of manufacturing cushion members.

2. Description of the Related Art

There are numerous situations where it is necessary or desirable to deliver a flow of breathing gas non-invasively to the airway of a user, i.e., without intubating the user or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping. Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient.

Traditional cushion members for patient interface devices include a sealing portion that is structured to engage the face of the patient in order to provide a seal therewith, as well as a body portion that is structured to provide support to the sealing portion. Known drawbacks of traditional cushion members include discomfort, undesirable red marks formed on the face of the patient, and leaks due to overstretching of the cushion member. More specifically, when pressure support therapy is being delivered, moisture in the breathing gas causes traditional cushion members to undesirably stretch, such that the integrity of the seal between the patient and the cushion member is compromised.

SUMMARY OF THE INVENTION

Accordingly, it is an object of the present invention to provide a cushion member for a mask structured to be worn on a face of a user. The cushion member includes a cushion portion having a sealing portion and a body portion extending from the sealing portion, the sealing portion being structured to engage the face of the user; and at least one mesh member embedded in at least one of the sealing portion and the body portion.

It is yet another object of the present invention to provide a method of manufacturing a cushion member comprising a method of manufacturing a cushion member comprising the steps of providing at least one mesh member; and overmolding a cushion portion on the at least one mesh member, the cushion portion having a sealing portion and a body portion extending from the sealing portion, the sealing portion being structured to engage a face of a user, the at least one mesh member being embedded in at least one of the sealing portion and the body portion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
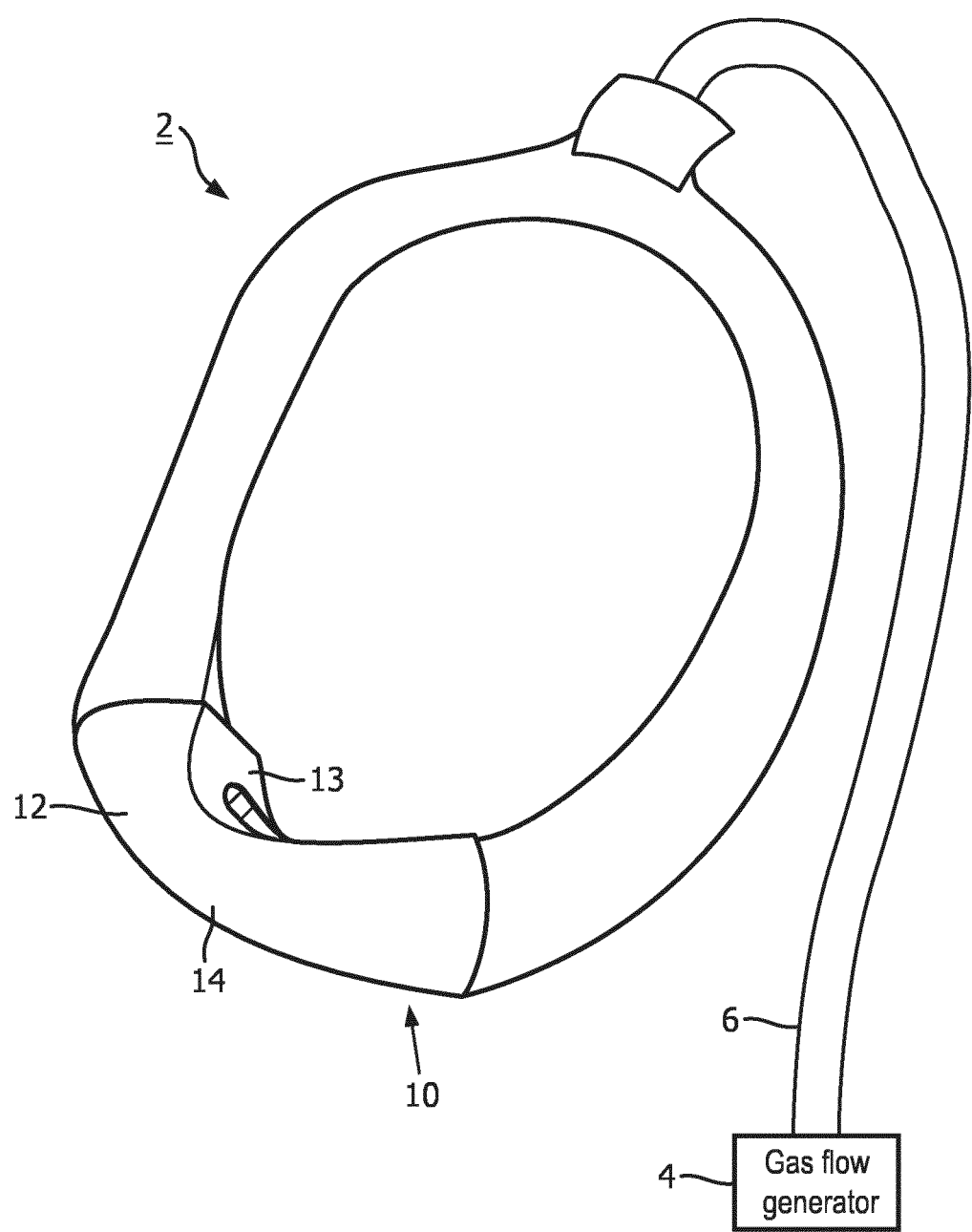
FIG. 1 is a simplified isometric view of a pressure support system, in accordance with a non-limiting embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, left, right, upper, lower, front, back, on top of, and derivatives thereof, relate to the orientation of the elements shown in the drawings and are not limiting upon the claims unless expressly recited therein.

As used herein, the term "mesh member" shall mean a component having a plurality of thru holes through which a viscous elastomeric material can permeate and/or flow in order that a mechanical bond is formed between the mesh member and the elastomeric material. A mesh member may be, for example and without limitation, a material consisting of a network of interlaced or otherwise entangled natural or artificial fibers, threads, or wires. A mesh member may also be, for example and without limitation, a perforated sheet of a material such as metal or plastic.

As used herein, the phrase "mechanical bond" shall mean a bond formed as a result of the curing (i.e., solidifying) of a material, such as a monomer, a polymer, and a mixture of a monomer and a polymer (e.g., without limitation, an elastomeric material such as silicone), to a mesh member. For example and without limitation, a bond formed when a viscous elastomeric material flows through a mesh member and is thereafter cured is a mechanical bond. As used herein, the term "embedded" shall mean enclosed and/or encapsulated on all sides.

FIG. 1 is a schematic diagram of a pressure support system 2 in accordance with one non-limiting embodiment of the disclosed concept. Pressure support system 2 includes a gas flow generator 4 (shown in simplified form), a gas delivery conduit (e.g., without limitation, hose 6, shown in simplified form), and a cushion member 10 for a mask structured to be worn on a face of user, such as a patient interface device. Gas flow generator 4 is structured to generate a flow of breathing gas to be delivered to an airway of the user, and may be a blower used in a conventional CPAP or bi-level pressure support device. Hose 6 fluidly couples gas flow generator 4 to cushion member 10, which is structured to engage the face of the user. In this manner, hose 6 allows gas flow generator 4 to deliver the flow of breathing gas to the airway of the user.

Figure 2:
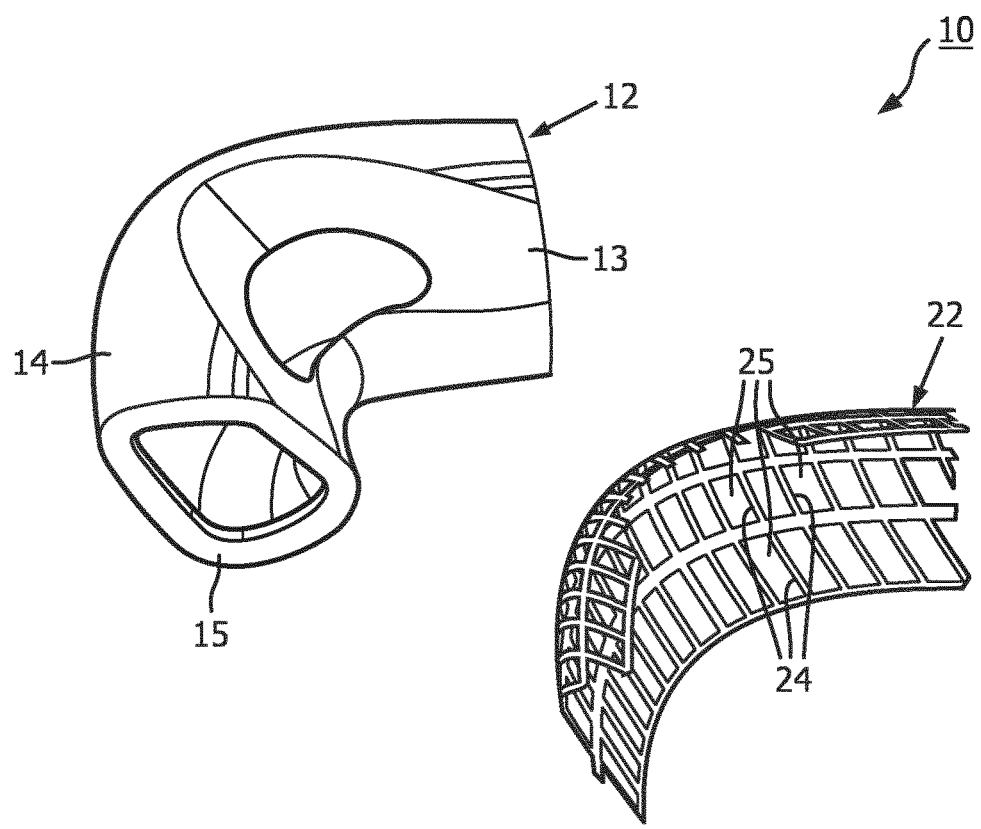
FIG. 2 and FIG. 3 are different exploded isometric views of a cushion member for the pressure support system of FIG. 1.
Figure 3:
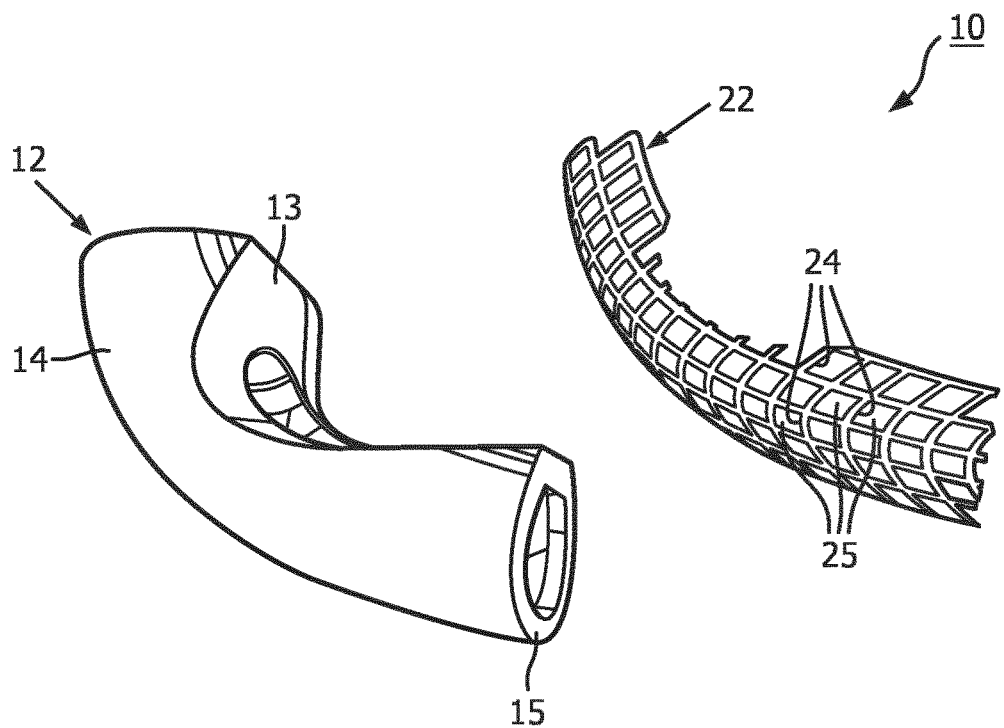

FIG. 2 and FIG. 3 show rear and front exploded isometric views, respectively, of cushion member 10. As shown, cushion member 10 includes a cushion portion 12 and a mesh member 22 that, as described herein, is embedded within cushion portion 12. Cushion portion 12 has a sealing portion 13 and a body portion 14 extending from sealing portion 13. Sealing portion 13 is structured to engage the face of the user in order to provide a seal therewith and allow gas flow generator 4 to effectively deliver the breathing gas to the user.

In accordance with the disclosed concept, mesh member 22 is embedded in at least one of sealing portion 13 and body portion 14. In the example depicted in FIG. 2 and FIG. 3, mesh member 22 is structured to be embedded within body portion 14. More specifically, mesh member 22 has a plurality of edge portions 24 that each define a respective thru hole 25. In the exemplary embodiment, during manufacturing of cushion member 10, cushion portion 12 is overmolded on mesh member 22 such that the viscous elastomeric material (e.g., without limitation, silicone) comprising cushion portion 12 flows, or permeates, through the thru holes 25 defined by edge portions 24 in order that mechanical bonds are formed between the viscous elastomeric material and edge portions 24 when the elastomeric material has cured. That is, cushion portion 12 extends through each of the plurality of thru holes 25 of mesh member 22 in order to be mechanically bonded to mesh member 22.

Additionally, when the elastomeric material of cushion portion 12 has cured, resulting body portion 14 has an embedding portion (generally indicated with reference numeral 15) and mesh member 22 is embedded within embedding portion 15. Embedding mesh member 22 within embedding portion 15 provides significant mechanical advantages for cushion member 10. For instance, in one example embodiment, mesh member 22 is made of a first material and cushion portion 12 is made of a second material different than the first material. The first material of mesh member 22 may be, for example and without limitation, a fabric material and/or a metallic material, while the second material of cushion portion 12 may be, for example and without limitation, an elastomeric material. The first material of mesh member 22 may have a modulus of elasticity less than the second material of cushion portion 12. The difference in materials and moduli of elasticity, combined with the mechanical bond between cushion portion 12 and edge portions 24, advantageously causes cushion member 10 to experience reduced elongation when subjected to tensile loads. In other words, mesh member 22 limits the stretch of cushion member 10 when cushion member 10 is subjected to tensile loads. As a result, cushion member 10 is structured to maintain a relatively strong seal and cause less red marks with users over time, as compared to prior art cushion members (not shown). Furthermore, moisture that accumulates during pressure support therapy will not significantly compromise the integrity of cushion member 10, which is an advantage over prior art cushion members.

Additionally, embedding mesh member 22 within cushion portion 12 significantly improves the ability of cushion member 10 to withstand tearing after repeated use. More specifically, mesh member 22 limits the stretch of cushion portion 12 to below its tear threshold. Also, if a tear does begin to form in cushion portion 12, mesh member 22 provides a physical bather to prevent propagation of the tear.

Figure 4:
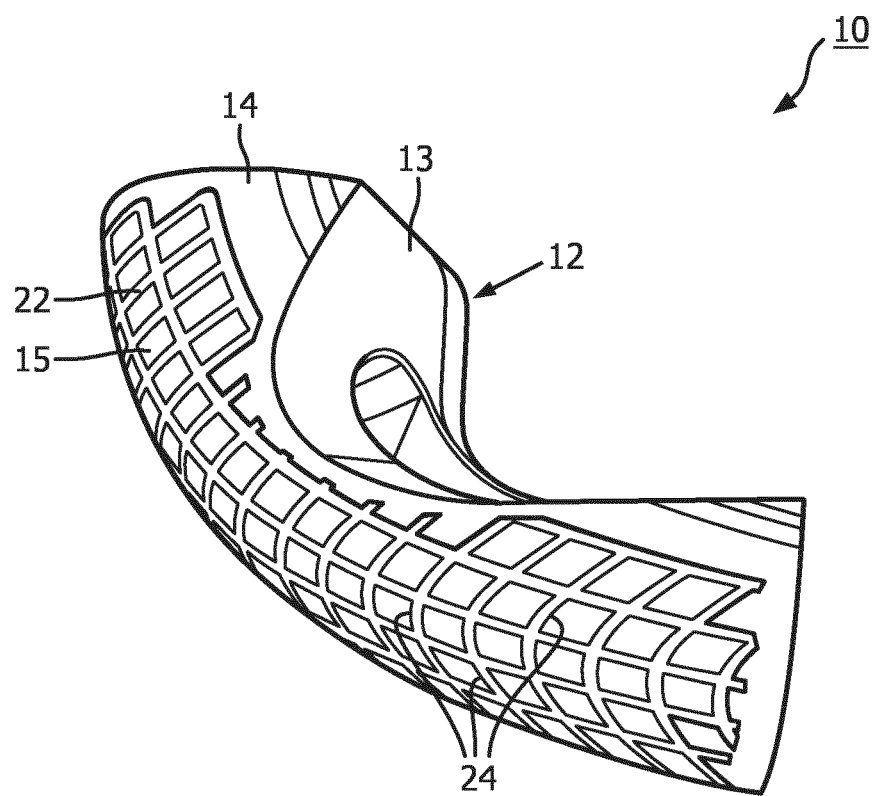
FIG. 4 is an isometric view of the cushion member of FIG. 2 and FIG. 3, modified such that the mesh member is on an exterior portion of the cushion portion for purposes of illustration only.

As shown in FIG. 4, which depicts mesh member 22 slightly offset from cushion portion 12 for purposes of illustration only, mesh member 22 has substantially the same shape as embedding portion 15. Accordingly, mesh member 22 is relatively flexible such that during manufacturing, when the viscous elastomeric material that comprises cushion portion 12 cures, mesh member 22 becomes shaped substantially the same as embedding portion 15. In this manner, mesh member 22 advantageously assists cushion portion 12 in retaining its shape.

Mesh member 22 has been described herein as being embedded within embedding portion 15 of body portion 14, and not being embedded in sealing portion 13. However, it will be appreciated that a similar suitable alternative mesh member (not shown) may be embedded within a different embedding portion of body portion 14, and/or may be embedded within sealing portion 13. That is, a similar suitable alternative cushion member (not shown) may include any number of mesh members embedded anywhere within a respective cushion portion in order to perform the desired function of providing improved mechanical advantages as described above.

Figure 5:
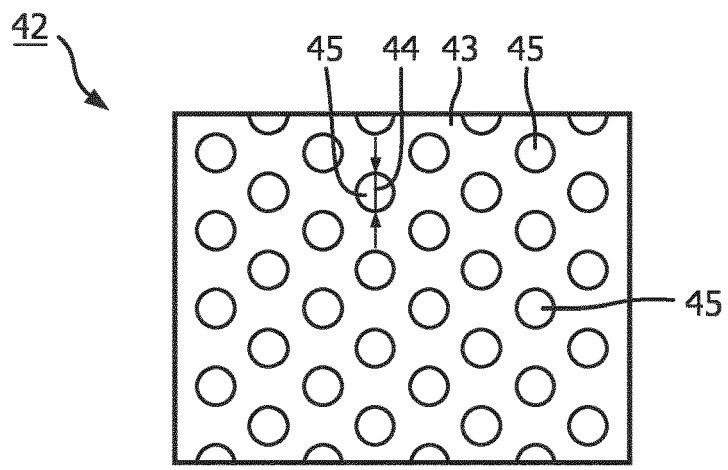
FIGS. 5-8 are simplified elevation views of alternative mesh members, in accordance with non-limiting alternative embodiments of the disclosed concept.
Figure 6:
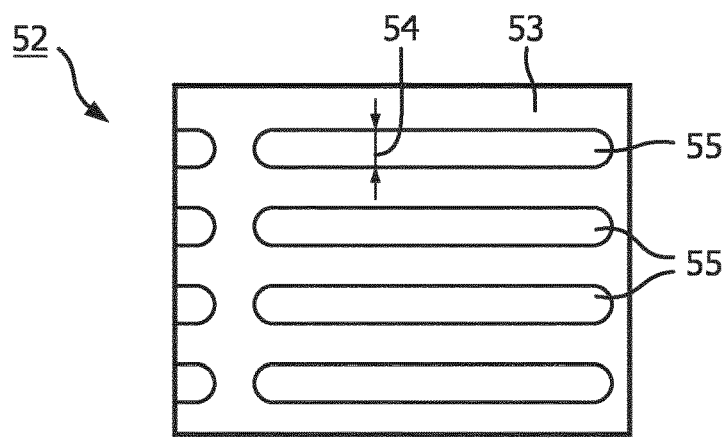
Figure 7:
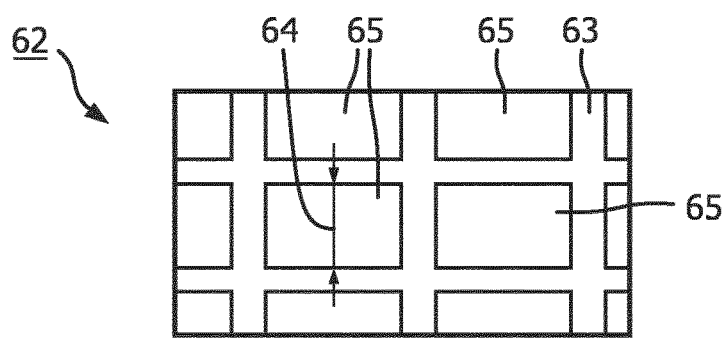
Figure 8:
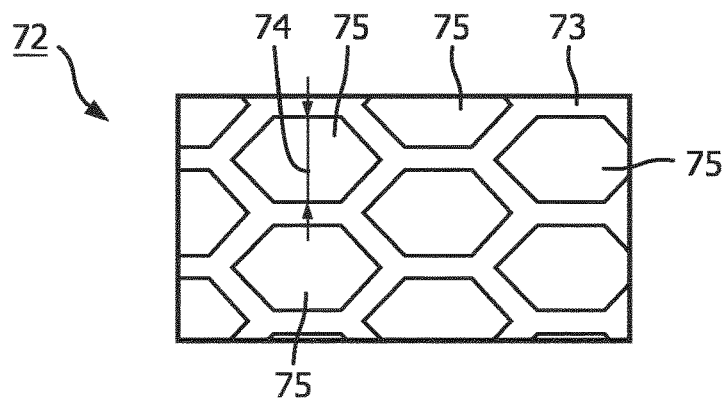

FIGS. 5-8 show alternative mesh members 42,52,62,72, respectively, that may be embedded in cushion portion 12 in place of mesh member 22, and/or in addition to mesh member 22, in accordance with non-limiting alternative embodiments of the disclosed concept. Referring to FIG. 5, mesh member 42 has a body 43 having a number of circular-shaped thru holes 45. FIG. 6 shows mesh member 52 having a body 53 having a number of elongated slots 55. FIG. 7 shows mesh member 62 having a body 63 having a number of square-shaped thru holes 65, and FIG. 8 shows mesh member 72 having a body 73 having a number of hexagonal-shaped thru holes 75.

Thru holes 45 each have a respective diameter 44, slots 55 each have a respective height 54, thru holes 65 each have a respective side length 64, and thru holes 75 each have a respective height 74. Diameters 44, heights 54, 74, and side lengths 64 are each greater than about 0.003 millimeters. The inventors have found that diameters, heights, and side lengths less than 0.003 millimeters are impermeable to the flow of viscous elastomeric material, such as during a molding operation. In this manner, because of the size of holes 45, 65, 75 and slots 55, viscous elastomeric material is advantageously able to permeate therethrough and allow for a relatively strong mechanical bond. Additionally, bodies 43, 53, 63, 73 of mesh members 42, 52, 62, 72 may be made of any material suitable to perform the desired function of forming mechanical bonds with elastomeric materials and becoming shaped according to corresponding embedding portions. For example and without limitation, bodies 43, 53, 63, 73 of mesh members 42, 52, 62, 72 may be made of metallic materials, such as perforated metal sheets.

Accordingly, it will be appreciated that a method of manufacturing cushion member 10 includes the steps of providing at least one mesh member 22, 42, 52, 62, 72, and overmolding cushion portion 12 on mesh member 22, 42, 52, 62, 72. The overmolding step further includes the steps of extending body portion 14 and/or sealing portion 13 through mesh member 22, 42, 52, 62, 72 in order to mechanically bond body portion 14 and/or sealing portion 13 to mesh member 22, 42, 52, 62, 72, and extending body portion 14 and/or sealing portion 13 through the plurality of thru holes of mesh member 22, 42, 52, 62, 72.

Although the disclosed concept has been described in association with cushion member 10 being a nasal cushion member, it is within the scope of the disclosed concept to employ any number of mesh members (not shown) substantially the same as mesh members 22, 42, 52, 62, 72 in suitable alternative cushion members (not shown) for patient interface devices, including, but not limited to, pillows style cushion members, nasal/oral cushion members, and full face cushion members. The disclosed concept may also be used with alternative mask devices, including, without limitation, scuba masks and firefighter masks. It is also within the scope of the disclosed concept to embed any number of mesh members (not shown) substantially the same as mesh members 22, 42, 52, 62, 72 in other suitable members, including, but not limited to, heart rate monitors and/or other devices worn on the wrist or elsewhere, elastomeric frames for patient interface devices, and/or straps for swimming goggles.

Figure 9:
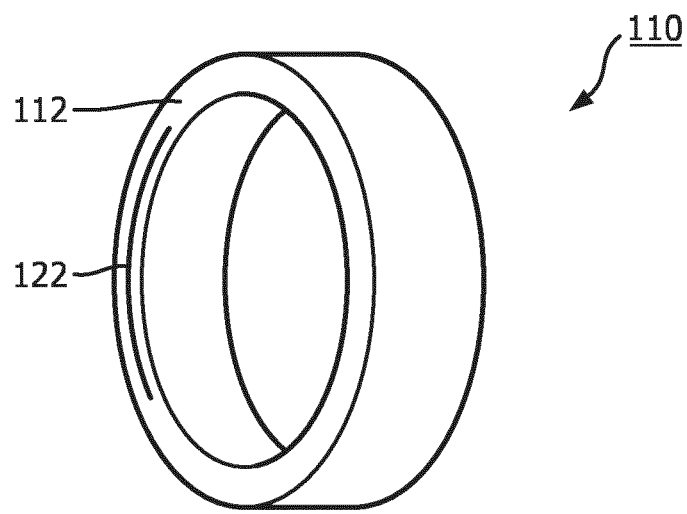
FIGS. 9-11 are simplified isometric views of alternative cushion members, in accordance with non-limiting alternative embodiments of the disclosed concept.
Figure 10:
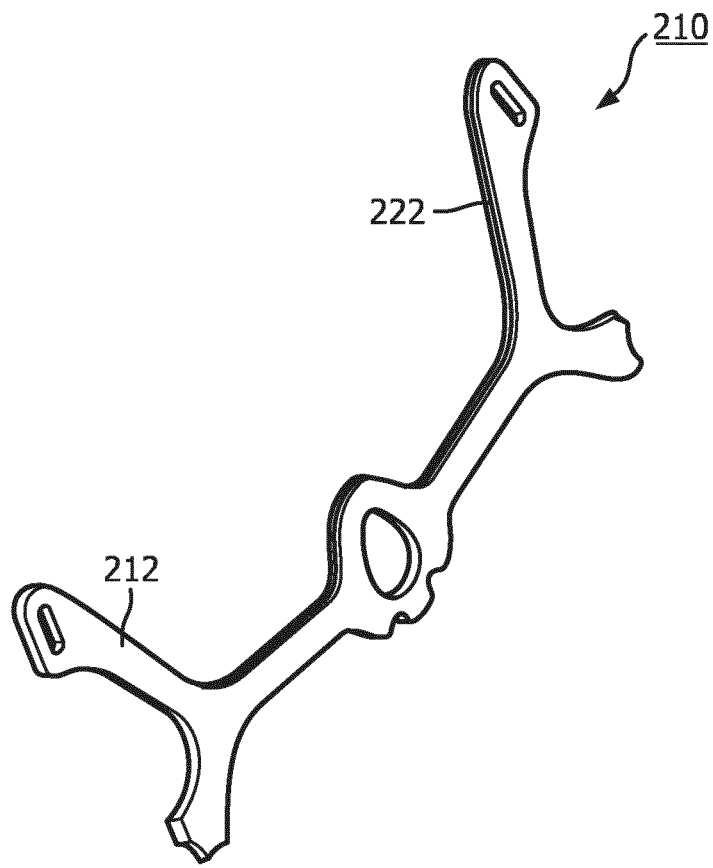
Figure 11:
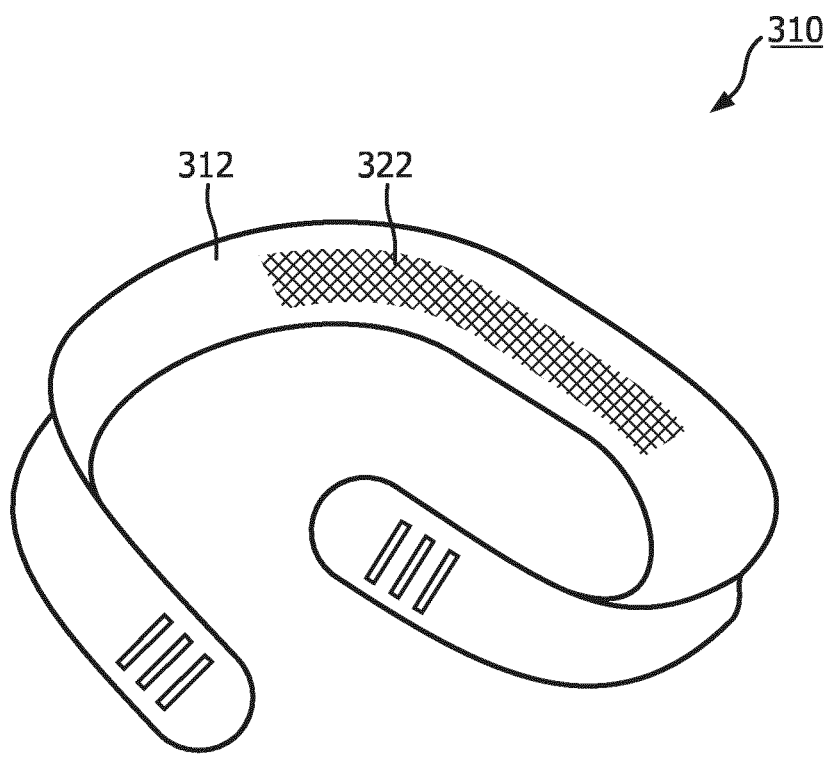

For example, FIGS. 9-11 show simplified views of alternative non-limiting embodiments of the disclosed concept. FIG. 9 shows an example heart rate monitor 110 structured to be worn on a wrist of a user. Heart rate monitor 110 includes a body portion 112 and a mesh member 122 (depicted with a curvilinear indicia) embedded in body portion 112. FIG. 10 shows a mask frame 210 for a patient interface device. Mask frame 210 includes a frame member portion 212 and a mesh member 222 (depicted with a curvilinear indicia) embedded in frame member portion 212. FIG. 11 shows a strap member 310 for use with a pair of swimming goggles (not shown). Strap member 310 includes a body portion 312 and a mesh member 322 embedded in body portion 312. Mesh members 122, 222, 322 may be substantially the same as mesh members 22, 42, 52, 62, 72, discussed hereinabove. Accordingly, by incorporating mesh members 122,222,322 in the respective portions 112, 212, 312 in substantially the same manner as mesh members 22, 42, 52, 62, 72 and cushion portion 12, the aforementioned mechanical advantages discussed above in association with cushion member 10 likewise apply to heart rate monitor 110, mask frame 210, and strap member 310.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion member for a mask structured to be worn on a face of a user, the cushion member comprising:
    a cushion portion having a sealing portion, a body portion extending from the sealing portion, a first orifice for allowing a gas to flow into the cushion portion and a second orifice for allowing the gas to flow out of the cushion portion and to the user's airways, the sealing portion being structured to engage the face of the user; and
    at least one mesh member embedded within at least one of the sealing portion and the body portion, wherein the at least one mesh member is made of a fabric material, wherein the cushion portion is made of an elastomeric material, and wherein the at least one mesh member does not occlude the second orifice such that the gas will not pass through the at least one mesh member when the gas flows out of the cushion portion.

2. The cushion member according to claim 1, wherein the at least one of the sealing portion and the body portion extends through the at least one mesh member; and wherein the at least one of the sealing portion and the body portion mechanically bonds to the at least one mesh member.

3. The cushion member according to claim 2, wherein the at least one mesh member has a plurality of thru holes; and wherein the at least one of the sealing portion and the body portion extends through each of the plurality of thru holes.

4. The cushion member according to claim 3, wherein the plurality of thru holes are selected from the group consisting of circular-shaped thru holes having a diameter greater than about 0.003 millimeters, elongated slots having a height greater than about 0.003 millimeters, square-shaped thru holes having a side length greater than about 0.003 millimeters, and hexagonal-shaped thru holes having a height greater than about 0.003 millimeters.

5. The cushion member according to claim 1, wherein the cushion portion has a first modulus of elasticity; and wherein the at least one mesh member has a second modulus of elasticity less than the first modulus of elasticity.

6. The cushion member according to claim 1, wherein the at least one of the sealing portion and the body portion comprises a first embedding portion;
wherein the at least one mesh member comprises a first mesh member embedded in the first embedding portion; and wherein the first mesh member is shaped substantially the same as the first embedding portion.

7. The cushion member according to claim 1, wherein the mask is a patient interface device.

8. A method of manufacturing a cushion member comprising the steps of:
providing at least one mesh member; and
overmolding a cushion portion on the at least one mesh member, the cushion portion having a sealing portion, a body portion extending from the sealing portion, a first orifice for allowing a gas to flow into the cushion portion and a second orifice for allowing the gas to flow out of the cushion portion and to the user's airways, the sealing portion being structured to engage a face of a user, the at least one mesh member being embedded within at least one of the sealing portion and the body portion, wherein the at least one mesh member is made of a fabric material, and wherein the cushion portion is made of an elastomeric material, and wherein the at least one mesh member does not occlude the second orifice such that the gas will not pas through the at least one mesh member when the gas flows out of the cushion portion.

9. The method according to claim 8, wherein the overmolding step further comprises:
extending the at least one of the sealing portion and the body portion through the at least one mesh member in order to mechanically bond the at least one of the sealing portion and the body portion to the at least one mesh member.

10. The method according to claim 9, wherein the at least one mesh member has a plurality of thru holes; and wherein the overmolding step further comprises: extending the at least one of the sealing portion and the body portion through each of the plurality of thru holes.

11. The method according to claim 10, wherein the plurality of thru holes are selected from the group consisting of circular-shaped thru holes having a diameter greater than about 0.003 millimeters, elongated slots having a height greater than about 0.003 millimeters, square-shaped thru holes having a side length greater than about 0.003 millimeters, and hexagonal-shaped thru holes having a height greater than about 0.003 millimeters.

12. The method according to claim 8, wherein the cushion portion has a first modulus of elasticity; and wherein the at least one mesh member has a second modulus of elasticity less than the first modulus of elasticity.

13. The method according to claim 8, wherein the at least one mesh member is made of a first material; and wherein the cushion portion is made of a second material different than the first material.

* * * * *